United States Patent [19]

Pender

[11] Patent Number: 4,712,537

[45] Date of Patent: Dec. 15, 1987

[54] APPARATUS FOR TREATING RECURRENT EAR INFECTIONS

[76] Inventor: Daniel J. Pender, 325 E. Park Ave. - Suite 1, Long Beach, N.Y. 11561

[21] Appl. No.: 895,917

[22] Filed: Aug. 13, 1986

[51] Int. Cl.⁴ .............................................. A61B 1/22
[52] U.S. Cl. .................................. 128/9; 128/303.15; 124/76
[58] Field of Search ................ 128/9, 303.1, 395–398, 128/303.15, 305, 310, 329 R, 746, 765, 6; 124/64–67, 73, 74, 76, 77; 434/18, 24

[56] References Cited

U.S. PATENT DOCUMENTS

| 1,775,140 | 9/1930 | Platou | 128/9 |
| 3,020,912 | 2/1962 | Chester | 128/310 |
| 3,530,860 | 9/1970 | Majoros | 128/305 |
| 3,596,653 | 8/1971 | Hotchkiss | 128/9 |
| 3,913,584 | 10/1975 | Walchle et al. | 128/305 |
| 4,622,967 | 11/1986 | Schachar | 128/9 |
| 4,625,706 | 12/1986 | Turner | 124/67 |
| 4,641,663 | 2/1987 | Juhn | 128/765 |

Primary Examiner—Max Hindenburg
Attorney, Agent, or Firm—Myron Amer

[57] ABSTRACT

A method and apparatus for treating ear infections in which a straight linear path is established from an external position to a specific target site on the eardrum. Thereafter a laser beam is caused to be emitted along the established path to impinge upon the eardrum to create a hole at the target site. Immediately thereafter, a hollow, tubular drainage missile is caused to be projected along the same established path into the hole formed at the target site to seat therein. The missile maintains the hole open for the drainage of the middle ear for so long as the physician deems necessary.

7 Claims, 11 Drawing Figures

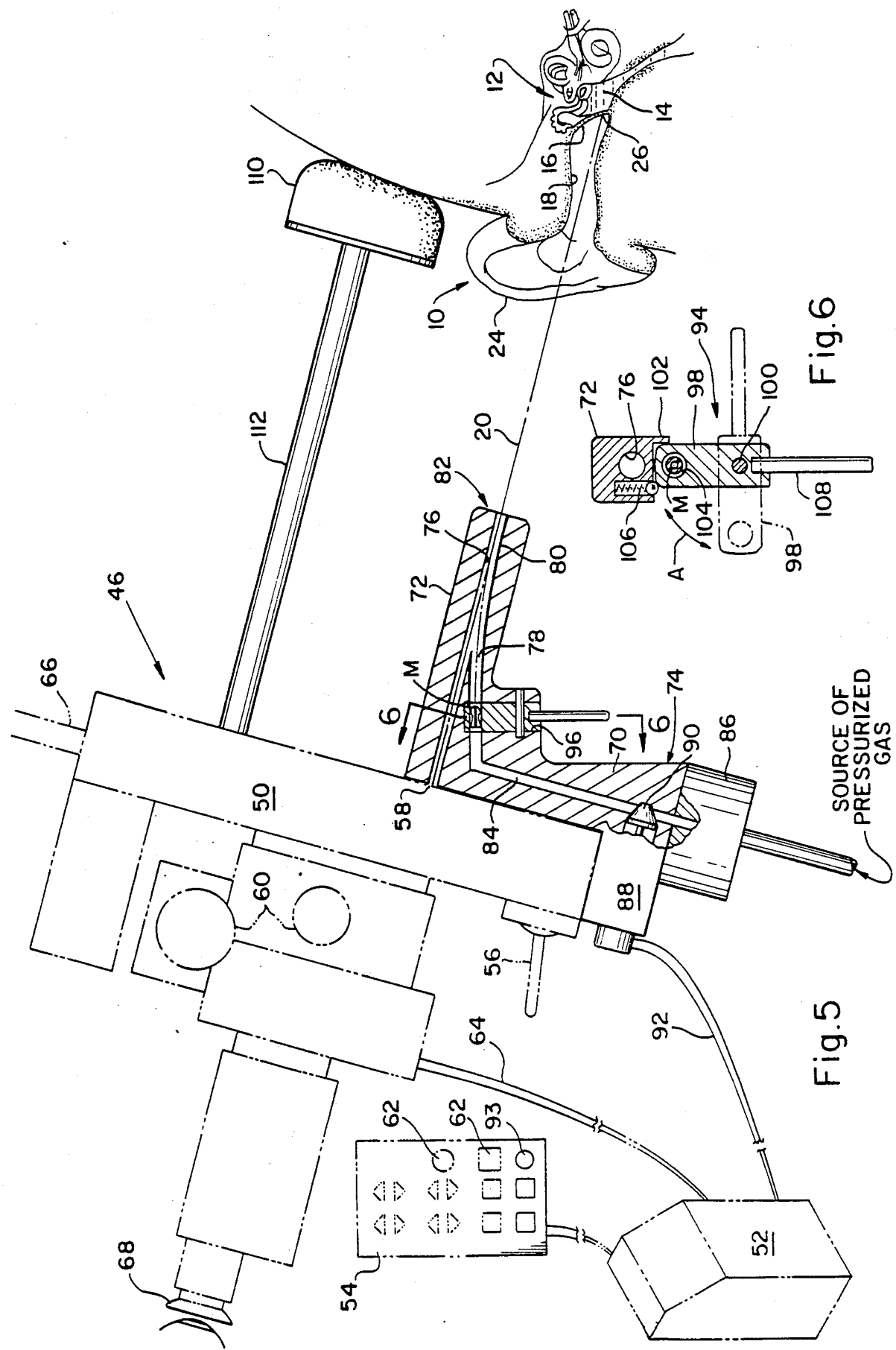

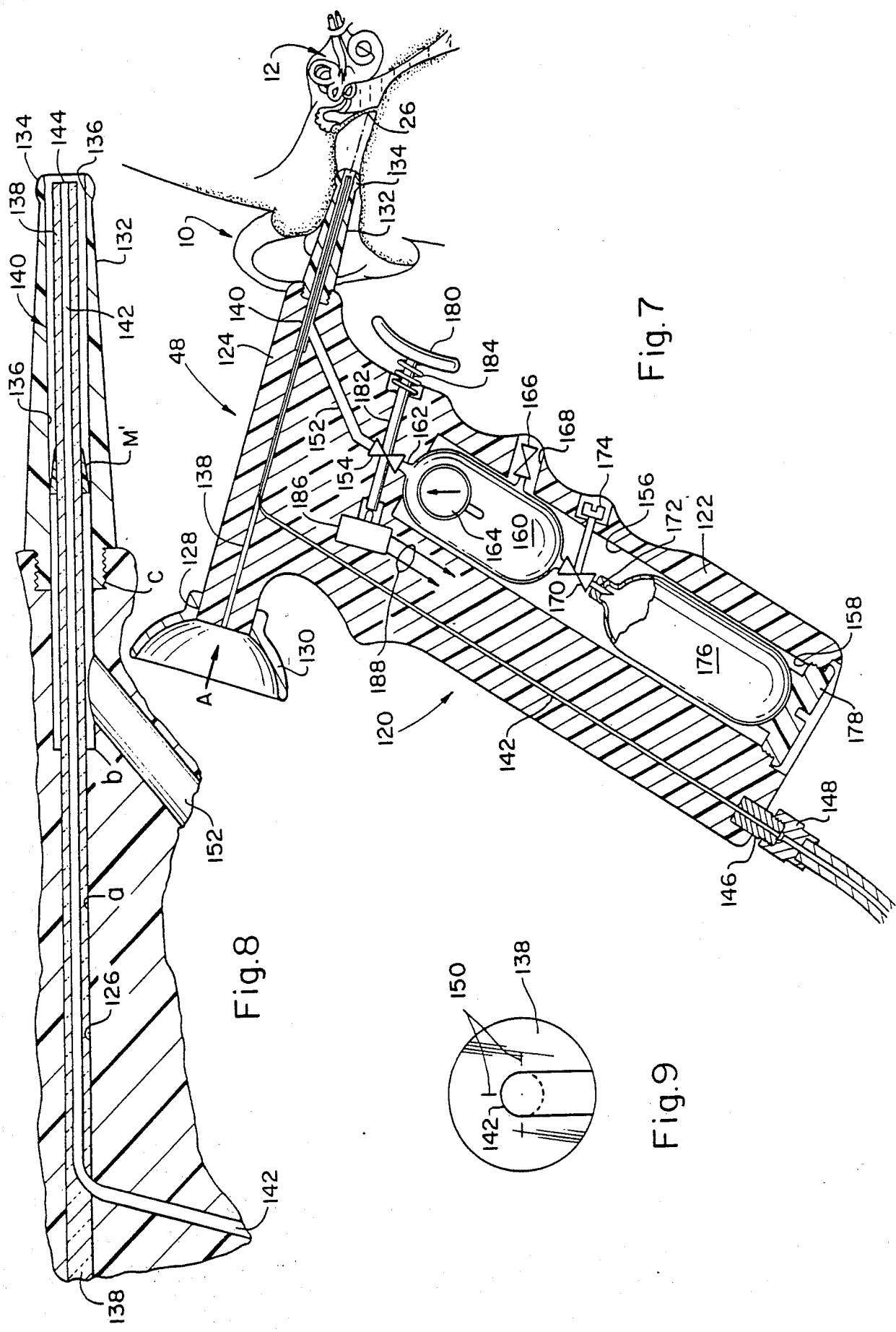

APPARATUS FOR TREATING RECURRENT EAR INFECTIONS

BACKGROUND OF THE INVENTION

The present invention relates to a method and apparatus for treating persistant ear infections.

Recent advancements in the treatment of many physical dysfunctions and illnesses have employed laser technology, i.e. the use of high intensity light to incise, cauterize or otherwise treat internal tissues and organs. The use of laser technology has become quite common for the treatment of eye, knee and bladder conditions and recently there has been a suggestion to use this technology in the treatment of recurring ear effusions and infections, where large bodies of fluid collect in the middle ear forming a host for the growth of bacteria and an impediment to hearing. An article, appearing in "LASERS: Lightwave of the Future", edited by Allan Mauer, Arco Publishing Inc., 1982 page 11, reported an experiment by Dr. Richard Goode, Associate Professor of Surgery at Stamford University, in which a laser beam was employed to pierce a patient's eardrum permitting the draining of the fluid from the middle ear. This technology was reported as being inherently less painful, quicker and more easily healable than the prior techniques which were based upon knife or needle surgery.

The techniques reported by Dr. Goode have not, however, been widely adopted since several still unsolved problems exist. An initial problem lies in the absence of suitable equipment and the means necessary for aiming and delivering the laser beam to the exact spot on the eardrum to provide the most effective drainage hole, while a second, equally significant problem lies in the maintenance of the hole formed, by the laser beam, open for a sufficiently long time to permit complete drainage of the underlying fluid collection. The use of conventional drainage tubes requires general anesthesia and manual insertion in the case of children, and such is usually preferred in a hospital operating room.

It is an object of the present invention to provide a method and an apparatus for the solution of each of the above problems.

It is a specific object of the present invention to provide an improved method and apparatus for laser surgery for treating ear infections which allows for quick and precise opening of the eardrum and complete drainage of the middle ear, and the attendant elimination of associated infection.

It is another specific object to provide a method and apparatus by which not only is the laser beam accurately aimed and delivered to the eardrum but in addition to which a novel drainage missile is propelled into the hole thus formed in the eardrum so that the hole can be maintained open over an extended period of time allowing full drainage to take place. The drainage missle can thus remain embedded for as long as the physician deems necessary without any subsequent surgical procedure to maintain the hole open.

These objects, as well as other objects and advantages will be apparent from the following disclosure of the present invention.

SUMMARY OF THE INVENTION

According to the present invention a surgical procedure is provided for treating ear infections in which a straight linear path is established from an external position to a specific target site on the eardrum, and thereafter a laser beam is caused to be emmited along the established path to ultimately impinge upon the eardrum to create a hole at the target site. Immediately thereafter, a hollow, tubular drainage missile is caused to be projected along the same established path into the hole formed at the target site to seat therein, so as to maintain the hole open for the drainage of the middle ear for so long as the physician deems necessary.

It should be noted that the laser pulse and drainage missile are emitted from the oto-injectoscope device simultaneously. Because the laser pulse travels faster than the missle, the laser pulse reaches and vaporizes the target point on the eardrum several milliseconds before arrival and penetration of the missile. The vaporation produced by the laser pulse creates a non-bleeding opening as well as a vapor bubble on the middle ear side of the opening. This permits the dart to lodge dry and clean, unclogged with neither blood or middle ear fluid.

Further, according to the present invention an oto-injectoscope apparatus is provided for carrying out the foregoing method and procedure which provides a body having means enabling the sighting and aiming of the laser beam along a specifically established path, means for delivering the laser beam along the path so established, and thereafter means for causing the propulsion of a tubular drainage missile along the same path, all within an unbroken sequence of operation and without the need to remove or exchange any portion of the apparatus during the procedure.

In one aspect of the present invention the oto-injectoscope is constructed as an auxiallary unit for a microscope laser delivery system of conventional design. In another aspect the oto-injectoscope is constructed as an a hand held unit which may be used separately and which is portable and highly maneuverable.

In yet another feature of the present invention, a missile or dart shaped hollow plug is provided which may be propelled into the eardrum hole to remain fixed therein during the entire course of fluid drainage.

Full details of the present invention are set forth in the following disclosure and are illustrated in the accompanying drawings.

BRIEF DESCRIPTION OF THE DRAWINGS

In the drawings:

FIG. 5 is a side elevational view, partly schematic and partly in section, showing a form of apparatus embodying the present invention and which may be applied to a laser delivery system having a microscope aiming device;

FIG. 6 is a sectional view of the device taken along lines 6—6 of FIG. 5;

FIG. 7 is a side elevational view partially in section of a embodiment of the present invention;

FIG. 8 is an enlarged view of the barrel and muzzle sections of the apparatus shown in FIG. 7, and;

FIG. 9 is an end view taken in the direction of arrow A in FIG. 7.

DESCRIPTION OF THE INVENTION

Figure 1A:
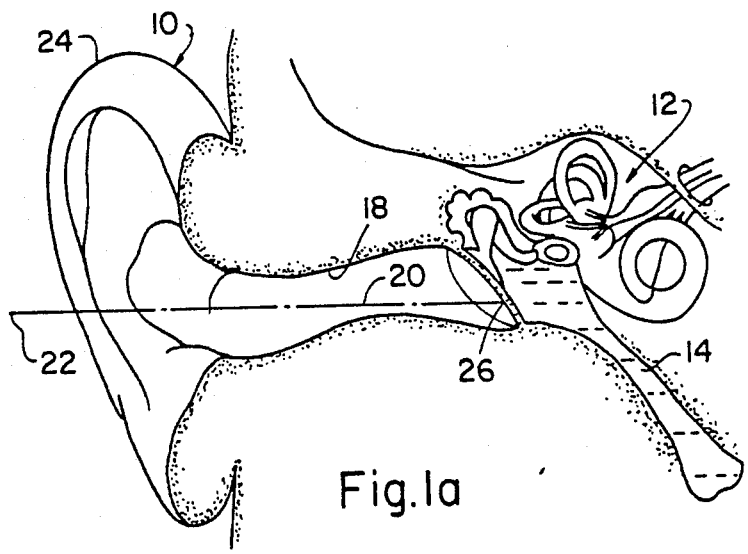
FIGS. 1a, 1b and 1c are sequential views illustrating the operational steps in carrying out the present invention.
Figure 1B:
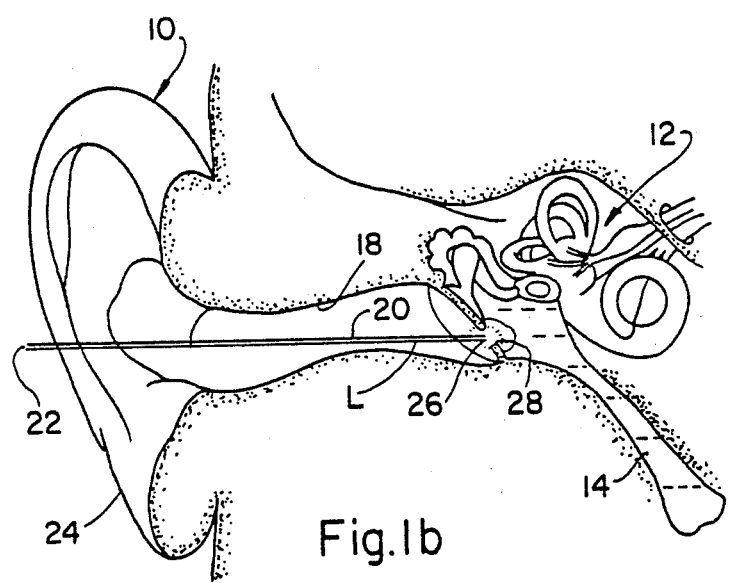
Figure 1C:
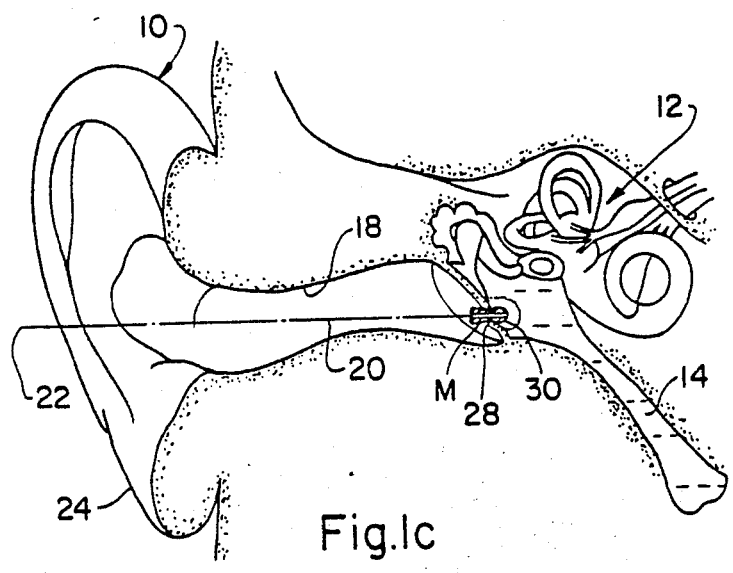

A brief discussion of FIGS. 1a through 1c is initially provided to give both an overall general background, as well as to point out several specific areas of advancement provided by both the method and apparatus of the present invention. In these figures an ear, generally depicted by the numeral 10 is shown having an infection in its middle ear 12. The infection is characterized by the concentration of fluid 14 within the middle ear 12 pressing on the eardrum 16 separating the middle ear 12 from the external auditory canal 18.

In the first step of the present invention (FIG. 1a), a line of sight is established using a conventional eyepiece, microscope or the like, along which a free unencumbered straight line of sight path 20 is established. The path 20 extends through the auditory canal 18, from some fixed point 22, exterior of the outer ear 24, to a target point 26 on the surface of the eardrum 16. In the second step, shown in FIG. 1b, a laser beam L of controlled intensity and spot size is caused to pass through the auditory canal 18 along (i.e. coincidental to) the established path 20 to impinge exactly on the target point 26 resulting in the vaporization of the eardrum 16 at this point and the creation of a relatively enlarged hole 28. The hole 28 allows the middle ear 12 to communicate freely with the auditory canal 18 so that the fluid 14 may drain therefrom which results when the vacuum pressure holding the fluid in the middle ear is vented. Immediately thereafter, as seen in FIG. 1c, a hollow tubular drainage missile M is propelled along the same established path 20, preferably utilizing an air or fluid pressure propulsion system to lodge securely in the hole 28 formed in the eardrum 16.

Figure 2:
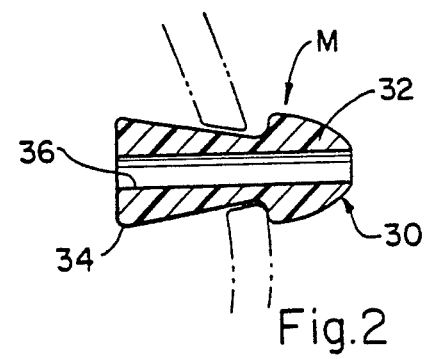
FIG. 2 is an enlarged cross-sectional view of a drainage missile employed in the present invention showing its positioning within the eardrum.

As seen in FIG. 2, the drainage missile M, shown in place within the hole 28 formed within the eardrum 16, has a dart-like shape with an enlarged pointed head 30. The exterior surfaces of the missile may be formed of soft-resilient material 32 so as to reduce possible damage to the eardrum and insure passage of the drainage missile into and out of the eardrum 16 without other damage to it. The tail 34 of the drainage missile M flares conically outwardly toward the rear providing a shape adapted to slow and retard the drainage missile from passing completely through the eardrum 16. The drainage missile M is provided with a smooth axial throughbore 36 which may be advantageously lined with less elastic material so that this bore will retain its shape allowing free communication between the external and middle ears. If desired, the drainage missile can be made of two layers of material; an inner layer of less resilient and elastic material, and an outer layer of more elastic and resilient material.

Figure 3:
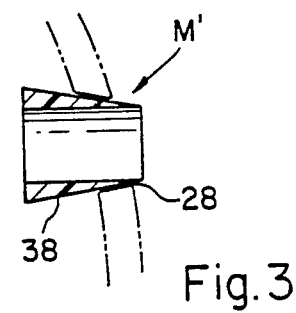
FIG. 3 is a cross sectional view of another form of a drainage missile employed in the present invention.
Figure 4:
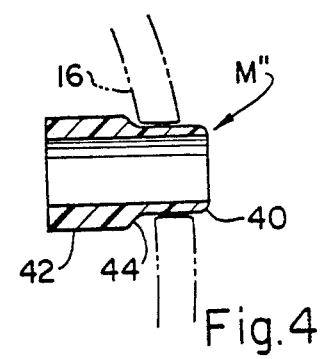
FIG. 4 is a cross sectional view of yet another form of drainage missile.

The drainage missile may take other shapes as seen in FIGS. 3 and 4. In FIG. 3 the drainage missile M' is a truncated cone having a smooth conical exterior 38 tapering to a degree so as to create sufficient friction between its surface and the edges of the hole 28 to cause this missile M' to firmly seat within the hole 28 in the absence of any head portion. In FIG. 4, the drainage missile M" is in the form of a two step cylinder having a smaller outer diameter section 40 at its forward end and a larger outer diameter section 42 at its rear end connected by a shoulder 44 which acts to prevent this missile M" from passing completely through the eardrum 16. It will be noted in all of the forms, the drainage missile is hollow having a smooth uniform inner diameter.

It will be observed that in the employment of the present method no mechanical instrument is caused to intrude against the eardrum and thus trauma to the eardrum or other parts of the ear are avoided. Conventional treatment of this problem in children requires general anesthesia, and its attendant health risks, in order to manually insert such pressure equalizing tubes. The hole in the eardrum is made solely by the less painful or intrusive burst of laser energy which can be precisely controlled and regulated and even subjected to preprogrammed microprocessor control.

Normally, the laser formed hole would close in a matter of days or weeks. Using a hollow tube or dart inserted in the opening will keep it open for a protracted period of time (e.g., months, as is often desirable). At present, placement of such a tube or dart must be done manually, often with a need for general anesthesia because of the pain of such manipulation.

After healing of the middle ear and the drainage of all fluid, the drainage missile may be easily removed by the physican using conventional forceps or tongs, thereafter allowing the hole to close under normal conditions.

Two forms of oto-injectoscope apparatus for carrying out the foregoing method are shown in FIGS. 5 through 9. In FIGS. 5 and 6 the apparatus is developed as an auxiliary unit generally depicted by the numeral 46 attachable to a conventional laser delivery and microscope unit, while in FIGS. 7 to 9 the apparatus is developed as an independent hand held unit in the form of a gun, generally depicted by the numeral 48 connected solely by conduits to a laser power source and control system.

As seen in FIGS. 5 to 6 the auxiliary oto-injectoscope is applied as an auxiliary unit to the conventional microscope laser delivery system (shown in dotted lines) such as that marketed by the Laserscope Corporation under the trademark OMNIPLUS. The basic delivery system comprises a turret, generally depicted by the numeral 50 in which an optical microscope system is housed, a power and light source console 52 and a control panel 54. The turret 50 is provided with a system which includes an aiming control in the form of a stick 56, which enables the physician to precisely aim the microscope at a selected target through an orifice 58 through which the beam of the laser passes. Several control knobs 60 are provided so that adjustment can be made to the focal length and eventual spot size of the specific target hole to be formed, as developed through the microscope.

The control panel 54 includes manually operable switches 62 for activating the laser light source, the electric power source and for controlling the aiming and emission of the laser beam through the orifice 58 throughout each of the surgical steps. The console 52 contains a microprocessor, which is preprogrammed to insure proper sequencing, power control and complete operation of the laser delivery system, as well as the electrical light power sources. The console 52, control panel 54 and the microscope turret 50 are interconnected by wire and fiber optic conduits 64. The turret 50 is hung from an overhead support or gantry illustrated by the connecting arm 66. This enables the physician to easily manipulate the turret 50, while looking through the eyepiece 68 and yet be free from any concern regarding its stability once placed into a given position.

Further details of the basic laser delivery system including the microscope so far described are not believed necessary for a full understanding of the present invention. However, if such details are indeed required, the same are incorporated herein by reference to the commercially available units sold under the trademark OMNIPLUS, to the aforementioned Laserscope Coporation, or to any one of the other commercial systems.

To provide this otherwise conventional laser delivery system with the means for carrying out the present invention, the auxiliary oto-injectoscope 46 is mounted to the front face of the microscope turret 50 in any manner as by the use of screws, bolts or the like. The unit is pistol shaped being formed with an elongated barrel member 72 extending generally horizontal (i.e. perpendicular to the front face of the turret 50) and a generally vertical depending handle member 74. The barrel member 72 is formed with a small diameter main firing bore 76 axially aligned with the laser aiming and delivery orifice 58 so that the sight line of the physician, and the eventual laser beam path passes through the barrel 72 coaxially with the main firing bore 76 and identical to the sight and aiming line 20, as previously described. A second or auxiliary bore 78 having a dog-leg shape, passes upwardly through the housing 70 with its upper or shorter leg 80 curving in a smooth arc to merge coaxially with the main firing bore 76 inwardly from the free end of the barrel to provide a muzzle section 82 commonly aligned with the sight and aiming line 20. The longer leg 84 of the auxiliary bore 78 extends outwardly from the bottom end of the housing 70 through an air pressure regulating device 86 to a source of high pressure such as a $CO_2$ cannister or container (not shown). The drainage missile M is loadable within the short leg 80, in a manner to be discussed hereinafter.

Extending laterally through the lower end of the housing 70 is a poppet valve assembly 88, the head 90 of which is biased to normally extend into and occlude the auxiliary bore 84 from communication with the air regulator 86. The poppet valve 88 is preferably a spring-biased solenoid (not-shown), selectively actuatable to retract the poppet head 90 on receipt of a signal, thereby permitting a burst of pressurized air to pass through the auxiliary bore 78 to provide the propulsive force necessary to shoot the drainage missile M outwardly of the muzzle 82. To this end the solenoid is connected by an electrical conduit 92 to the microprocessor in the console 52, wherein its operation is controlled as a part of the program contained therein. To this end the control panel is provided also with manual control 93 for firing the poppet valve as may be desired by the physican, as well.

To supply the drainage missile M to the auxiliary bore 78, a breech mechanism generally depicted by the numeral 94 is built into a slot 96 formed in the housing 70. As seen in FIG. 6, the breech mechanism 94 comprises a simple block 98 rotatable at its lower end about a pivot pin 100 so that the block 98 can be swung, as seen by the double arrow A between an open position (dotted lines) and a closed position (full lines). The closed position is defined by a depending flange or lip 102 formed adjacent the slot 96 on the far side of the barrel 72. The breech block 98 is provided with a small bore 104 into which the drainage missile M is manually inserted. The form and shape of the drainage missile M particularly if it has an outer softer resilient surface, insures a close but slidable fit in the auxiliary bore 78 so that the propulsive force acts positively on the drainage missile. As seen in FIG. 5, the small breech bore 104 is located so that it aligns itself with the auxiliary bore 78 when the block 98 is placed in the closed position, and has a snug-fit in the slot 96 so as to prevent any escape of pressurized air from the auxiliary bore 78 upon release of the poppet valve 88.

A spring loaded ball detent 106 is located in a recess in the barrel 72 directly above the slot 96 and acts on the edge of the breech block 98 to prevent its inadvertent opening once the breech block 98 is placed in the closed position. The breech block 98 is further provided with a small depending handle 108 enabling the physician to manually open and close the breech block 98.

Lastly, as seen in FIG. 5, a head rest 110 may be mounted at the end of a shaft 112 extending from the frontal face of the turret 50 so as to make contact with the surface of the patient's head to thereby enable the physician to steady the turret 50 and stabilize the sight and aiming lines during the several steps of the surgical procedure.

In operation, the auxiliary unit 46 presents no difficulty whatsoever. In preparing for the use of this unit, the physican first chooses the missile and loads the same in the breech thereafter closing the breech. The physican then programs the laser delivery system for the level of energy, spot size etc and then places the unit in position relative to the patient. Thereafter, its use follows the steps of the method described earlier, in that the physican first establishes a sight line, utilizing the microscope system in the turret, thereafter causes the burst of laser energy to vaporize the hole in the eardrum and middle ear, and simultaneously causes the propulsion of the missile M toward and into the eardrum.

In the second embodiment shown in FIG. 7-9, the one piece hand held oto-injectoscope unit 48 comprises a body 120 in the form of a contoured pistol grip 122 and an integrally formed barrel 124. The barrel 124 has an axial bore 126 of three stepped diameter portions a, b and c as seen in detail in FIG. 8. The smallest diameter portion a extends from the rear end of the barrel 128 inwardly, most of the length of the barrel. The central and slightly larger diameter portion b extends further terminating at the larger diameter portion c which is internally threaded. The rear end 128 of the barrel 124 is enlarged to form a boss on which a resilient eye piece 130 is fixed. At the forward end of the barrel 124, a tubular ear piece 132 is removably attached to the internally threaded larger diameter portion c of the bore 126. The ear piece 132 is provided with a forward tip 134 adapted to enter through the outer ear 24 into the auditory canal 18 to rest in close proximity to the eardrum 16 of the patient. The ear piece 132 is further provided with an inner bore 136 having the same diameter as the central portion of the barrel bore 126 so that in effect a smooth extension is achieved at the central portion c.

Embedded firmly within the smallest diameter portion a of the barrel bore 126 is a sighting lens 138, such as a "Hopkins rod lens" which transmits to the viewer a clear and somewhat enlarged image of the eardrum. The rod lens 138 has a smooth uniform exterior surface which extends forwardly from its embedment in the bore portion a, cantilevered through the central diameter portion b and the bore 136 of the extending ear piece 132. Note that portion b and the bore 136 form an annular chamber 140 about the rod lens 138. A missile M is slidably placed over the surface of the rod lens 138 and positioned to the rear of the forward tip 134 of the ear piece. Preferably the missile M makes sliding contact with both the surface of the rod lens 138 and the innersurface of the bore 136 of the extending ear piece 132 so as permit the propulsion without air leakage.

Extendin upwardly through the pistol grip 122 is light transmissive fiber optic bundle 142 which passes into the rod lens 138 forwardly of the eye piece 130. The fiber optic bundle 142 is embedded through remaining forward portion of the rod lens 138 so that it extends coaxially with it to its forwardmost tip 144. The opposite end of the fiber optic bundle 142 extends through the pistol grip and out from its bottom end through a male optical connector 146 to which it is removably coupled, by its counter part female connector 148 a fiber optic cable, which extends to the source of laser light.

As seen in FIG. 9, the view through the eye piece 130 is coaxial being made through the sighting rod lens 138 onto the selected target point 26 on the eardrum. The target point 26 can be initially illuminated to enable proper viewing by providing the fiber optic bundle 142 with a low intensity light and only later vaporized and the eardrum perforated by a burst of high energy laser light. The eye piece 130 or the lens 138 can be provided with cross hairs 150, or other indicia enabling the physican to more readily establish a proper sighting path and focus upon the target point.

To effect propulsion of the missile M, a bore 152 extends at an angle to the annular chamber 140 through the pistol grip 122 terminating in a manually operable air valve 154 which lies adjacent to an enlarged oblong cavity 156. The cavity 156 is open at its bottom 158 and has retained at its upper end a pressure vessel 160 which has an outlet 162 connected directly to the air valve 154. The pressure vessel 160 is provided with a gauge 164 which is preferably visible from the exterior as well as with a relief valve 166 set within a recess 168 on the surface of the pistol grip so as to allow relief of the pressure vessel when and if necessary. A charging valve 170 is connected to the lower end of the pressure vessel 160. The charging valve 170 has a pin inlet 172 and a control knob 174 which extends outwardly from the pistol grip 122 so as to be manipulable from the outside.

A standard size pressurized $CO_2$ cartridge 176 is also received within the cavity 156 and is held firmly within the cavity by shaped plug 178 which threadly closes the bottom opening 158. When the closing plug 178 is screwed into the bottom opening 158 it presses the cartridge 176 onto the inlet pin 172 of the charging valve 170 so that communication between the charging valve 170 and the cartridge 176 is assured.

Mounted on the pistol grip 122 for easy manipulation is a trigger 180 having an elongated shaft 182 movably extending into the pistol grip 122. The trigger 180 is biased in a nominal outward condition by a spring 184. The end of the shaft 182 lies in opposition to a micro switch 186 which is normally in open condition and is closed only by depression of the trigger 180. The micro switch 186 leads via a wire cable 188 to the laser power system so as to conduct the signal from the micro switch 186 to the power system for its activation. The shaft 182 concurrently passes in engagement with the control mechanism of the air valve 154 whereby the air valve 154 may be opened also by a depression of the trigger 180 thereby permitting pressurized gas from the pressure vessel 160 through the bore 152 into the annular chamber 140 of the barrel 126. The trigger shaft 182 and its connection to both the micro switch 186 and the air valve 154 is arranged, such that depression of the trigger causes near simultaneous activation of laser pulse emission and drainage missile firing, thereby ensuring that both laser pulse and missile are following the same trajectory as the selected line of sight. This assures that the missle will indeed lodge in the laser created hole in the eardrum.

The oto-injectoscope just described may be easily employed by the physican simply by connecting the laser cables and micro switch cables to the appropriate power sources in the control console and the pistol grip carried by the physican to and from the patient. Since this hand held unit is not dependant upon any given basic microscope and laser delivery system, the cables may be of any length and may be attached to any conventional system. The air propulsion system is built into the pistol grip and therefore does not require a large source such as a compressor or the like. The ability, furthermore, to insert the ear piece into the auditory canal allows placing the tip as close to the eardrum as possible thus reducing the distance of travel of the missile to a minimun.

It will be seen that, as in the earlier embodiment, the present unit provides for a coincidential sight, line and laser path and coaxial missile path. The missile itself may be loaded onto the rod lens either before or after the ear piece is threaded onto to the barrel and may be made by hand with or without assistance of any tool although because of the extremely small size of the missile and the barrel bore a loading or ram rod may be desirable. Dimensionally, the over all outer diameter of the ear piece may be about 4 mm and thus be convenient for the general size range of auditory ear canals; the inner diameter of the ear piece tip and of the central portion of the barrel bore may be about 3 mm; while, the outer diameter of the rod lens may be about 2 mm. With these dimensions, the tubular missile has an interior diameter slightly larger than 2 mm and exterior diameter slightly less than 3 mm to ensure sliding action within the barrel bore over the lens. The other sizes and dimensions of the pistol grip barrel etc are neither critical nor material.

Standard laser power sources and control consoles as well as computer programs or the like may be employed and reference to the aforementioned OMNIPLUS units ca be made for these components.

Various modifications, changes and embodiments have been described. Other such modifications, changes and embodiments will be apparent to those skilled in the present art. Accordingly, it is intended that this disclosure be taken as illustrative only and not limiting of the scope of the invention.

What is claimed is:

1. An apparatus for treating ear infections comprising a body mounted on a turret and having a main bore extending linearly from a fixed opening through which a sighting and delivery of laser energy passes axially enabling the location and formation of a hole by vaporization of a selected target site on an eardrum, an auxillary bore connected at one end to a source of air under pressure and at its other end to said main bore, a breech block having a cylinder for receiving a missile to be positioned in said eardrum, said breech block being mounted in said body between an open position permitting loading of the missile therein and a closed position aligning the receiving cylinder in the breech block with the said auxiliary bore, and means for selectively controlling the passage of air through said auxiallary bore for propelling the missile into and through said main bore.

2. The apparatus according to claim 1 wherein said means and auxiliary bores are of equal diameter, and said auxiliary bore extends at an arc into said main bore at a distance to the rear of the forward tip of said main bore so that the auxiliary bore and the main bore are coincidental for a predetermined distance with said body.

3. The apparatus according to claim 1 including control means for automatically regulating the sighting and laser energy and for controlling the passage of air to provide the same in a predetermined sequence.

4. The apparatus according to claim 1 including a valve interposed between said breech block and said source of air under pressure, said valve being operable to normally occlude said auxiliary bore and being selectively operable to point a burst of air under pressure into said auxiliary bore.

5. The apparatus according to claim 1 including a tubular missile, said missile having an outside diameter substantially conforming to the diameter of said main bore, for sliding fit therein.

6. The apparatus according to claim 4 wherein said missile is dart shaped having a reduced forward end for insertion in the hole and an enlarged rear end preventing passage through the hole in said eardrum.

7. The apparatus according to claim 11 wherein said missile has a resilient elastic outer layer at least at its forward end.

* * * * *